United States Patent
Zhou et al.

(10) Patent No.: US 7,264,829 B2
(45) Date of Patent: Sep. 4, 2007

(54) MORINDA CITRIFOLIA LEAF EXTRACT COMPOSITIONS AND METHODS OF OBTAINING THE SAME

(75) Inventors: Bing-Nan Zhou, Pleasant Grove, UT (US); Afa Kehaati Palu, Orem, UT (US); Chen X. Su, West Jordan, UT (US); Claude Jarakae Jensen, Cedar Hills, UT (US); Stephen Story, Alpine, UT (US)

(73) Assignee: Tahitian Noni International, Inc., Provo, UT (US)

( * ) Notice: Subject to any disclaimer, the term of this patent is extended or adjusted under 35 U.S.C. 154(b) by 22 days.

(21) Appl. No.: 10/796,625

(22) Filed: Mar. 8, 2004

(65) Prior Publication Data

US 2005/0196476 A1 Sep. 8, 2005

(51) Int. Cl.
 *A61K 36/746* (2006.01)
 *A61K 36/00* (2006.01)
(52) U.S. Cl. ...................................................... 424/725
(58) Field of Classification Search .................... None
 See application file for complete search history.

(56) References Cited

U.S. PATENT DOCUMENTS 4,666,606 A * 5/1987 Heinicke .................... 210/632

\* cited by examiner

*Primary Examiner*—Patricia Leith
(74) *Attorney, Agent, or Firm*—Kirton & McConkie; Michael F. Krieger

(57) ABSTRACT

Methods and compositions relating to leaf extracts obtained from *Morinda citrifolia* leaves. Methods and compositions relating to a leaf serum created from combining leaf extract and fruit juice from the *Morinda citrifolia* L. plant. Methods and compositions relating to leaf extract compositions comprising one or more of the leaf extracts and leaf serums.

4 Claims, 1 Drawing Sheet

*Adenosine $A_{2A}$ Bioassay*

**Dry *Morinda citrifolia* leaves**
200.01 gm
↓ Percolated with EtOH
↓ Remove solvent EtOH Extract
26-2-1 = 22-84-1

*Adenosine $A_{2A}$ Bioassay:*
*inhibition @ 100 µg/mL: 68%*

20.41 gm (10.2%)

Took 14.25 gm
↓ Partition between Hexane-90% MeOH

| Hexane Fraction | 90% aq. MeOH fraction |
|---|---|
| 26-2-2 | 26-2-3 |
| 3.58 gm (25.3%) | 10.59 gm (74.7%) |
| *Adenosine $A_{2A}$ Bioassay:* | *Adenosine $A_{2A}$ Bioassay:* |
| *inhibition @ 100 µg/mL: 93%* | *inhibition @ 100 µg/mL: 75%* |

↓ cc on $SiO_2/CH_2Cl_2$-MeOH

| | 22-8-1 | 22-8-2 | 22-8-3 | 22-8-4 + 22-8-5 | 22-8-6 to 8 |
|---|---|---|---|---|---|
| Yield: | 1.2 | 14.6 | 2.7 | 29.2 | 37.4 mg |
| | 1.2% | 14.7% | 2.7% | 29.5% | 37.9% |
| *Adenosine $A_{2A}$ Bioassay:* inhibition @ 100 µg/mL: | NT | 2% | 86% | 61% | NT |

*FIG. 1*

MORINDA CITRIFOLIA LEAF EXTRACT COMPOSITIONS AND METHODS OF OBTAINING THE SAME

BACKGROUND

1. Field of the Invention

The present invention relates to compositions comprising *Morinda citrifolia* leaf extracts, and methods for obtaining the same. More particularly, the present invention relates to compositions and methods involving *Morinda citrifolia* leaf extracts that have been dried using alcohol or alcohol-based derivatives.

2. Background of the Invention and Related Art

The *Morinda citrifolia* L. or Indian Mulberry plant, a plant commonly found in the islands of the pacific, has a fruit which is known to provide many health benefits. The fruit has a very pungent aroma when ripe, apparently to attract fruit bats which are dispersal agents for the seeds.

SUMMARY AND OBJECTS OF EMBODIMENTS OF THE INVENTION

The present invention comprises various methods of producing leaf extracts from the leaves of the Indian Mulberry or *Morinda citrifolia* L. plant. In addition, the present invention comprises various methods for creating a leaf serum by combining the leaf extracts with fruit juice of the *Morinda citrifolia* plant. Methods of the present invention also include incorporating the leaf serum into a pharmaceutical leaf product ("pharmaceutical" herein referring to any drug or product designed to improve the health of living organisms such as a human beings or mammals, including nutraceutical products). Still further, the present invention comprises various leaf extract compositions, including leaf extracts, leaf serum, and pharmaceutical products having leaf serum incorporated therein.

Accordingly, it is an object of some embodiments of the present invention to provide a method for obtaining leaf extract from the leaves of the *Morinda citrifolia* L. plant.

It is another object of some embodiments of the present invention to provide a method for obtaining a leaf serum, the leaf serum created by combining leaf extract and fruit juice, both the extract and the juice being obtained from the *Morinda citrifolia* L. plant.

It is a further object of some embodiments of the present invention to provide various leaf extract compositions created from the leaves of *Morinda citrifolia* L. plant.

BRIEF DESCRIPTION OF THE DRAWING

FIG. 1 is a flow chart representing extraction methods and points where bioassays were performed on *Morinda citrifolia* leaf extracts.

DETAILED DESCRIPTION OF THE PREFERRED EMBODIMENTS

The present invention comprises various methods of producing leaf extracts from the leaves of the Indian Mulberry or *Morinda citrifolia* L. plant. In addition, the present invention comprises various methods for creating a leaf serum by combining the leaf extracts with fruit juice of the *Morinda citrifolia* plant. Methods of the present invention also include incorporating the leaf serum into a pharmaceutical leaf product ("pharmaceutical" herein referring to any drug or product designed to improve the health of living organisms such as a human beings or mammals, including nutraceutical products). Still further, the present invention comprises various leaf extract compositions, including leaf extracts, leaf serum, and pharmaceutical products having leaf serum incorporated therein. Further details of the present invention are described below.

In some embodiments of the present invention, the *Morinda citrifolia* leaf extracts are obtained using a highly technical and precise process. First, relatively dry leaves from the *Morinda citrifolia* L. plant are collected, cut into small pieces, and placed into a crushing device, preferably a hydraulic press, where the leaf pieces are crushed. The crushed leaf pieces are then percolated with an alcohol such as ethanol, methanol, ethyl acetate, or other alcohol-based derivatives using methods known in the art. Next, the alcohol and all alcohol-soluble ingredients are extracted from the crushed leaf pieces, leaving a leaf extract that is then reduced with heat to remove all the liquid therefrom. The resulting dry leaf extract will herein be referred to as the "primary leaf extract."

In some embodiments of the present invention, the primary leaf extract is pasteurized to at least partially sterilize the extract and destroy objectionable organisms. The primary leaf extract is pasteurized preferably at a temperature ranging from 70 to 80 degrees Celsius and for a period of time sufficient to destroy any objectionable organisms without major chemical alteration of the extract. Pasteurization may also be accomplished according to various radiation techniques or methods.

In some embodiments of the present invention, the pasteurized primary leaf extract is placed into a centrifuge decanter where it is centrifuged to remove or separate any remaining juice therein from other materials, including chlorophyll. Once the centrifuge cycle is completed, the leaf extract is in a relatively purified state. This purified leaf extract is then again pasteurized in a similar manner as discussed above to obtain a purified primary leaf extract.

Preferably, the primary leaf extract, whether pasteurized and/or purified, is further fractionated into two individual fractions: a dry hexane fraction, and an aqueous methanol fraction. This is accomplished preferably via a gas chromatograph containing silicon dioxide and $CH_2Cl_2$-MeOH ingredients using methods well known in the art. In some embodiments, the methanol fraction is further fractionated to obtain secondary methanol fractions. In some embodiments, the hexane fraction is further fractionated to obtain secondary hexane fractions.

One or more of the leaf extracts, including the primary leaf extract, the hexane fraction, methanol fraction, any of the secondary hexane or methanol fractions will preferably be combined with the fruit juice of the fruit of the *Morinda citrifolia* plant to obtain a leaf serum, the process of obtaining the fruit juice to be described further herein. In some embodiments, the leaf serum is packaged and frozen ready for shipment; in others, it is further incorporated into other products as explained next.

The leaf serum and/or any of the leaf extracts can be further incorporated into a pharmaceutical leaf product (again, "pharmaceutical" herein referring to any drug or product designed to improve the health of living organisms such as a human beings or mammals, including nutraceutical products). Examples of pharmaceutical leaf products may include, but are not limited to: intravenous products, topical dermal products, wound healing products, skin care products, hair care products, beauty and cosmetic products (e.g., makeup, lotions, etc.), burn healing and treatment products, first-aid products, antibacterial products, lip balms and ointments, bone healing and treatment products, meat tenderizing products, anti-inflammatory products, eye drops, deodorants, antifungal products, arthritis treatment products, muscle relaxers, toothpaste, and various nutraceutical and other products as will be further explained herein.

Any of the leaf extract compositions of the present invention—that is, any composition having the leaf extract from the *Morinda citrifolia* leaves, including but not limited to: the primary leaf extract itself, the hexane fraction, methanol fraction, the secondary hexane and methanol fractions, the leaf serum, or the pharmaceutical leaf product—can include various other ingredients. Examples of other ingredients include, but are not limited to: artificial flavoring, other natural juices or juice concentrates such as a natural grape juice concentrate or a natural blueberry juice concentrate; carrier ingredients; and others as will be further explained herein.

In some embodiments of the present invention, active ingredients or compounds within the *Morinda citrifolia* leaf extracts may be extracted out using various procedures and processes commonly known in the art. For instance, the active ingredients may be isolated and extracted out using alcohol or alcohol-based solutions, such as methanol, ethanol, and ethyl acetate, and other alcohol-based derivatives using methods known in the art. These active ingredients or compounds may be isolated and further fractioned or separated from one another into their constituent parts. Preferably, the compounds are separated or fractioned to identify and isolate any active ingredients that might help to prevent disease, enhance health, or perform other similar functions. In addition, the compounds may be fractioned or separated into their constituent parts to identify and isolate any critical or dependent interactions that might provide the same health-benefiting functions just mentioned.

Exemplary Ingredients and Forms for the Leaf Extract Compositions

The leaf extract compositions of the present invention may be formulated into any of a variety of compositions, including oral compositions, topical dermal solutions, intravenous solutions, and other products or compositions. As mentioned above, the leaf extract compositions can include a variety of ingredients.

In regards to oral compositions, these may take the form of, for example, tablets, lozenges, aqueous or oily suspensions, dispersible powders or granules, emulsions, syrups, or elixirs. Compositions intended for oral use may be prepared according to any method known in the art, and such compositions may contain one or more agents such as sweetening agents, flavoring agents, coloring agents, and preserving agents. They may also contain one or more additional ingredients such as vitamins and minerals, etc. Tablets may be manufactured to contain one or more leaf extracts or leaf serums in admixture with non-toxic, pharmaceutically acceptable excipients that are suitable for the manufacture of tablets. These excipients may be, for example, inert diluents, granulating and disintegrating agents, binding agents, and lubricating agents. The tablets may be uncoated or they may be coated by known techniques to delay disintegration and absorption in the gastrointestinal tract and thereby provide sustained action over a longer period. For example, a time delay material such as glyceryl monostearate or glyceryl distearate may be used.

Aqueous suspensions may be manufactured to contain the leaf extracts and/or leaf serum in admixture with excipients suitable for the manufacture of aqueous suspensions. Examples of such excipients include, but are not limited to: suspending agents such as sodium carboxymethyl-cellulose, methylcellulose, hydroxy-propylmethycellulose, sodium alginate, polyvinyl-pyrrolidone, gum tragacanth and gum acacia; dispersing or wetting agents such as a naturally-occurring phosphatide like lecithin, or condensation products of an alkylene oxide with fatty acids such as polyoxyethylene stearate, or condensation products of ethylene oxide with long chain aliphatic alcohols such as heptadeca-ethylene-oxycetanol, or condensation products of ethylene oxide with partial esters derived from fatty acids and a hexitol such as polyoxyethylene sorbitor monooleate, or condensation products of ethylene oxide with partial esters derived from fatty acids and hexitol anhydrides such as polyethylene sorbitan monooleate.

Typical sweetening agents may include, but are not limited to: natural sugars derived from corn, sugar beets, sugar cane, potatoes, tapioca, or other starch-containing sources that can be chemically or enzymatically converted to crystalline chunks, powders, and/or syrups. Also, sweeteners can comprise artificial or high-intensity sweeteners, some of which may include aspartame, sucralose, stevia, saccharin, etc. The concentration of sweeteners may be between from 0 to 50 percent by weight of the leaf extract composition, and more preferably between about 1 and 5 percent by weight.

Typical flavoring agents can include, but are not limited to, artificial and/or natural flavoring ingredients that contribute to palatability. The concentration of flavors may range, for example, from 0 to 15 percent by weight of the leaf extract composition. Coloring agents may include food-grade artificial or natural coloring agents having a concentration ranging from 0 to 10 percent by weight of the leaf extract composition.

Typical nutritional ingredients may include vitamins, minerals, trace elements, herbs, botanical extracts, bioactive chemicals, and compounds at concentrations from 0 to 10 percent by weight of the leaf extract composition. Examples of vitamins include, but are not limited to, vitamins A, B1 through B12, C, D, E, Folic Acid, Pantothenic Acid, Biotin, etc. Examples of minerals and trace elements include, but are not limited to, calcium, chromium, copper, cobalt, boron, magnesium, iron, selenium, manganese, molybdenum, potassium, iodine, zinc, phosphorus, etc. Herbs and botanical extracts may include, but are not limited to, alfalfa grass, bee pollen, *chlorella* powder, Dong Quai powder, Ecchinacea root, Gingko Biloba extract, Horsetail herb, Indian mulberry, Shitake mushroom, spirulina seaweed, grape seed extract, etc. Typical bioactive chemicals may include, but are not limited to, caffeine, ephedrine, L-carnitine, creatine, lycopene, etc.

The ingredients to be utilized in a topical dermal product may include any that are safe for internalizing into the body of a mammal and may exist in various forms, such as gels, lotions, creams, ointments, etc., each comprising one or more carrier agents. The ingredients or carrier agents incorporated into systemically (e.g., intravenously) administered compositions may also comprise any known in the art.

Obtaining the Fruit Juice from the *Morinda citrifolia* Plant for Incorporation into a Leaf-Extract Composition of the Present Invention The fruit of the *Morinda citrifolia* L. plant is for all practical purposes inedible. Thus, the fruit must be processed in order to make it palatable for consumption and suitable for inclusion in products used to treat ailments or diseases. In one process of producing *Morinda citrifolia* fruit juice, the fruit is either hand picked or picked by mechanical equipment. The fruit can be harvested when it is at least one inch (two to three centimeters) and up to twelve inches (twenty-four to thirty-six centimeters) in diameter. The fruit preferably has a color ranging from a dark-green through a yellow-green, and up to a white color—and gradations of color in between. The fruit is thoroughly cleaned after harvesting and before any processing occurs.

The cleaned fruit is then allowed to ripen or age from zero to fourteen days, but preferably for two to three days. The fruit is ripened by being placed on equipment so that the fruit does not contact the ground. The fruit is then preferably covered with a cloth or netting material during aging, but the fruit can be aged without being covered. When ready for further processing, the fruit is light in color—anywhere between a light-green, light-yellow, white, or translucent color. The fruit is inspected for spoilage or for excessive green color and firmness. Spoiled and hard green fruit is separated from the acceptable fruit.

The ripened and aged fruit is preferably placed in plastic lined containers for further processing and transport. The ripened fruit is left in the containers for zero to thirty days, but preferably for seven to fourteen days, and optionally under refrigerated conditions. The fruit is then unpacked from the storage containers and is processed through a manual or mechanical separator that separates the seeds and peel from the juice and pulp. In some embodiments, pulp is filtered out of the juice. In some processes of the present invention, the juice and pulp of the fruit are pureed into a homogenous blend to be mixed with other ingredients. The filtered juice is preferably heated and pasteurized at a minimum temperature of 181° F. (83° C.) or higher at up to 212° F. (100° C.).

As was just mentioned, the juice can be processed by separating the pulp from the juice. This can be done through filtering equipment that preferably comprises, but is not limited to: a centrifuge decanter; a screen filter with a size from one micron up to 2000 microns, but more preferably less than 500 microns; a filter press; reverse osmosis filtration; or any other standard commercial filtration devices. The operating filter presser preferably ranges from 0.1 psig up to about 1000 psig. The flow rate preferably ranges from 0.1 gpm up to 1000 gpm, and more preferably between 5 and 50 gpm.

The fruit juice obtained from one or more of the just-mentioned processes can then be further incorporated into any of the leaf extract compositions mentioned herein. It will be noted that some of the embodiments of the present invention contemplate obtaining the *Morinda citrifolia* fruit juice pre-made.

EXAMPLE

Adenosine $A_2A$ Bioassay

As illustrated in the accompanying drawing, a bioassay has been performed to determine the effect of some embodiments of the leaf extract compositions on the Adenosine A2A enzyme. The "26-2-1" and other similar numerals represent various embodiments of the leaf extracts or leaf extract compositions. It will be observed that the 22-84-1 embodiment inhibited the enzyme by 68%; the 26-2-2 by 93%; the 26-2-3 by 75%; and the 22-8-3 by 86%. This bioassay also illustrates how various embodiments of the leaf extract compositions of the present invention were obtained.

Unless otherwise indicated, any numbers expressing quantities of ingredients, reaction conditions, and so forth present in the specification or any claims or drawings are to be understood as being modified in all instances by the term "about." Accordingly, unless indicated to the contrary, the numerical parameters set forth herein are approximations that may vary depending upon the desired properties sought to be obtained by the present invention. At the very least, each numerical parameter should at least be construed in light of the number of reported significant digits and by applying ordinary rounding techniques.

Notwithstanding that any numerical ranges and parameters that set forth the broad scope of the invention are approximations, the numerical values set forth in the specific examples are reported as precisely as possible. Any numerical value, however, inherently contains certain errors necessarily resulting from the standard deviation found in their respective testing measurements.

While illustrative embodiments of the invention have been described herein, the present invention is not limited to the various preferred embodiments described herein, but includes any and all embodiments having modifications, omissions, combinations, adaptations, and/or alterations as would be appreciated by those in the art based on the present disclosure. The limitations in any claims are to be interpreted broadly based on the language employed in the claims and not limited to examples described herein, which examples are to be construed as non-exclusive. For example, in the present disclosure, the term "preferably" should be construed as meaning "preferably, but not limited to."

The present invention may be embodied in other specific forms without departing from its spirit or essential characteristics. The described embodiments are to be considered in all respects only as illustrative and not restrictive. The scope of the invention is, therefore, indicated by the appended claims, rather than by the foregoing description. All changes which come within the meaning and range of equivalency of the claims are to be embraced within their scope.

What is claimed is:

1. A method for preparing a *Morinda citrifolia* leaf serum comprising:
   a) obtaining crushed, dry *Morinda citrifolia* leaves,
   b) percolating said crushed, dry *Morinda citrifolia* leaves through alcohol to obtain a mixture of an alcohol fraction comprising alcohol-soluble ingredients of *Morinda citrifolia* leaves and a solid fraction containing *Morinda citrifolia* leaves,
   c) isolating the alcohol from the mixture of part (b) to obtain an alcohol extract of *Morinda citrifolia* leaves,
   d) fractionating the isolated alcohol extract of part (c) into two fractions: a dry hexane fraction and an aqueous methanol fraction, and
   e) combining said dry hexane fraction or said aqueous methanol fraction of part (d) with *Morinda citrifolia* fruit juice to make a leaf serum.

2. The method of claim 1, wherein the *Morinda citrifolia* fruit juice is obtained by processing fruit of a *Morinda citrifolia* L. plant.

3. The method of claim 1, wherein said dry *Morinda citrifolia* leaves are obtained by heating *Morinda citrifolia* leaves.

4. The method of claim 1 further comprising combining said leaf serum with a carrier to obtain a pharmaceutical leaf product.

* * * * *